United States Patent

Manfre et al.

[11] Patent Number: 6,127,515
[45] Date of Patent: *Oct. 3, 2000

[54] FUNCTIONALIZED RESIN FOR THE SYNTHESIS OF AMIDES AND PEPTIDES

[75] Inventors: Franco Manfre, Saint Maurice, France; Benoit J. Vanasse, Collegeville, Pa.; Richard F. Labaudiniere, Collegeville, Pa.; George C. Morton, Collegeville, Pa.

[73] Assignee: Aventis Pharmaceuticals Products Inc., Bridgewater, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/316,671

[22] Filed: May 21, 1999

Related U.S. Application Data

[63] Continuation of application No. PCT/US98/24509, Nov. 16, 1998.
[60] Provisional application No. 60/065,648, Nov. 18, 1997, abandoned.

[51] Int. Cl.[7] .................. C08G 73/00; C08G 69/26; A61K 38/00; C07K 16/00; C07K 17/00
[52] U.S. Cl. .................. 528/367; 528/368; 528/369; 528/310; 528/328; 528/332; 530/333; 530/334; 530/335; 562/442
[58] Field of Search .................. 528/367, 368, 528/369, 310, 328, 332; 530/333, 334, 335; 562/442

[56] References Cited

U.S. PATENT DOCUMENTS

| | | | |
|---|---|---|---|
| 4,769,445 | 9/1988 | Comstock et al. | 530/333 |
| 5,288,514 | 2/1994 | Ellman | 427/2 |
| 5,545,568 | 8/1996 | Ellman | 436/518 |
| 5,635,598 | 6/1997 | Lebl et al. | 530/334 |
| 5,684,131 | 11/1997 | Lebl et al. | 530/334 |

FOREIGN PATENT DOCUMENTS

| | | |
|---|---|---|
| WO96/26223 | 8/1996 | WIPO . |
| WO98/18754 | 5/1998 | WIPO . |
| WO98/29376 | 7/1998 | WIPO . |
| WO99/41216 | 8/1999 | WIPO . |

*Primary Examiner*—Duc Truong
*Attorney, Agent, or Firm*—Irving Newman; Peter Butch

[57] ABSTRACT

This invention is directed to a functionalized amino resin of formula

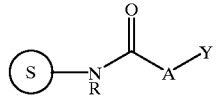

I wherein (S) is a solid support; R is H or alkyl; A is

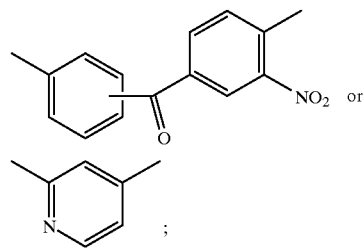

Y is OH or OCOR[1]; and R[1] is aliphatic or aromatic which is useful for the solid phase synthesis of amides, peptides and hydroxamic acids.

15 Claims, No Drawings

FUNCTIONALIZED RESIN FOR THE SYNTHESIS OF AMIDES AND PEPTIDES

CROSS REFERENCE TO RELATED APPLICATIONS

This application is a continuation application of International Patent Application No. PCT/US98/24509, filed Nov. 16, 1998, which is a continuation-in-part of U.S. patent application Ser. No. 60/065,648, filed Nov. 18, 1997, now abandoned.

FIELD OF THE INVENTION

This invention is directed to a functionalized resin and derivatives thereof and to its use in the solid phase synthesis of amides peptides and hydroxamic acids.

BACKGROUND OF THE INVENTION

Solid-phase synthetic techniques, in which a reagent is immobilized on a polymeric material which is inert to the reagents and reaction conditions employed, as well as being insoluble in the media used, are important tools for preparing of amides, peptides and hydroxamic acids. For solid phase peptide synthesis, a summary of the many techniques may be found in J. M. Stewart and J. D. Young, *Solid Phase Peptide Synthesis*, 2nd. Ed., Pierce Chemical Co. (Chicago, Ill., 1984); J. Meienhofer, *Hormonal Proteins and Peptides*, vol. 2, p. 46, Academic Press (New York), 1973; and E. Atherton and R. C. Sheppard, *Solid Phase Peptide Synthesis: A Practical Approach*, IRL Press at Oxford University Press (Oxford, 1989). For the use of solid phase methodology in the preparation of non-peptide molecules see Leznoff, C. C., *Acc. Chem. Res.*, 11 327–333 (1978).

A polymeric reagent has the advantage of ease of separation from low molecular weight reactants or products by filtration or selective precipitation. The polymeric reagent can also be used in excess to effect fast and quantitative reactions, or a large excess of reactants may be used to drive the equilibrium of the reaction towards product formation to provide essentially quantitative conversion to product. Further advantages of polymeric reagents is the fact that they are recyclable and that they lend easily to automated processes. In addition, supported analogs of toxic and odorous reagents are safer to use.

The use of functionalized polymers of formula

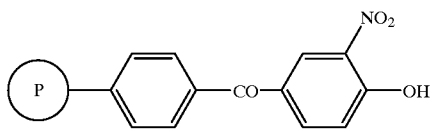

for peptide synthesis is described by Cohen, et al., *J. Org. Chem.*, 49 (5), 922–24 (1984).

The use of functionalized polymers of formula

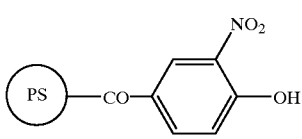

for peptide synthesis is described by A. Patchornik, *Makromol. Chem., Macromol Symp.* 70/71 455–457 (1993).

SUMMARY OF THE INVENTION

This invention is directed to a functionalized resin of formula I

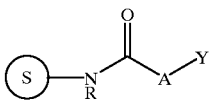

wherein (S) is a solid support;

R is H or alkyl;

A is

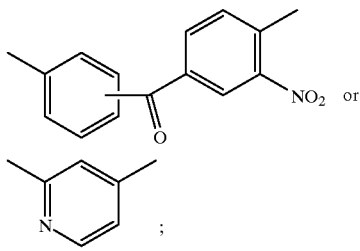

Y is OH or OCOR$^1$; and

R$^1$ is aliphatic or aromatic.

In another aspect, this invention is directed to a process for preparing an amide of formula

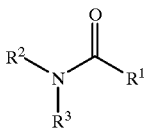

wherein

R$^1$ is aliphatic or aromatic; and

R$^2$ and R$^3$ are independently H, aliphatic or aromatic, comprising reacting a resin-bound activated ester compound of formula

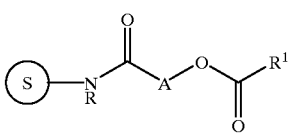

wherein (S) is a solid support;

R is H or alkyl; and

A is

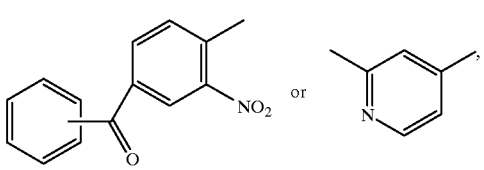

with an amine of formula HNR$^2$R$^3$.

DETAILED DESCRIPTION OF THE INVENTION

Definitions of Terms

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid Phase Peptide Synthesis*, 2nd. Ed., Pierce Chemical Co. (Chicago, Ill., 1984).

In addition, "solid support" includes a solid support as described above which is affixed to a second inert support such as the pins described herein which comprise a detachable polyethylene- or polyproylene-base head grafted with an amino functionalized methacrylate copolymer and an inert stem.

In addition, "solid support" includes polymeric supports such as the polyethylene glycol supports described by Janda et al., *Proc. Natl. Acad. Sci. USA*, 92, 6419–6423 (1995) and S. Brenner, WO 95/16918, which are soluble in many solvents but can be precipitated by the addition of a precipitating solvent.

"Resin" means a solid support as defined above which is chemically modified as is known in the art to incorporate a plurality of amino (—NHR) or aminomethyl (—CH$_2$NHR) groups. The amino groups or aminomethyl groups are covalently bound directly to the solid support or attached to the solid support by covalent bonds through a linking group. The resins used in preparing the functionalized resins of this invention are designated herein as

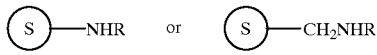

wherein R is H or alkyl and Ⓢ designates a solid support as defined herein to which the amino groups or aminomethyl groups are directly bound or the combination of a solid support and linking group.

"Amino resin" means a resin of formula

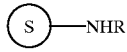

wherein R is defined herein.

"Aminomethyl resin" means a resin of formula

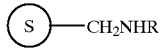

wherein R is defined herein. Representative aminomethyl resins include aminomethyl (polystyrene-polyoxyethylene) (NovaSyn® TG resin, available from Calbiochem-Novabiochem Corp. San Diego, Calif.), in which the aminomethyl group is attached through a polyoxyethylene linking group, and (aminomethyl) polystyrene (aminomethyl resin) in which the aminomethyl group is directly attached to the solid substrate:

aminomethyl (polystyrene-polyoxyethylane

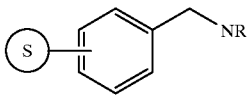

aminomethyl (polystyrene).

"Linking group" and "linker" mean a group through which the amino or aminomethyl functionality may be covalently linked to the solid support. The linking group generally comprises an inert polymeric material such as polyethylene glycol (PEG, also commonly referred to as polyoxyethylene).

"Amine protecting group" means an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, CF, for example, T. H. Greene and P. G. M. Wuts, Protective Groups in Organic Synthesis, 2nd edition, John Wiley & Sons, New York (1991), incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-rimethylsilylethxoycarbonyl, vinyloxycarbonyl, allyloxycarbonyl, t-butyloxycarbonyl (BOC), 1-dimethylpropynyloxycarbonyl, benzyloxycarbonyl (CBZ), p-nitrophenylsulfinyl, p-nitrobenzyloxycarbony, 2,4-dichlorobenzyloxycarbonyl, allyloxycarbonyl (Alloc), and the like.

"Carboxylic acid protecting group" and "acid protecting group" mean an easily removable group which is known in the art to protect a carboxylic acid (—CO$_2$H) group against undesirable reaction during synthetic procedures and to be selectively removable. The use of carboxylic acid protecting groups is well known in the art and many such protecting groups are known, CF, for example, T. H. Greene and P. G. M. Wuts, Protective Groups in Organic Synthesis, 2nd edition, John Wiley & Sons, New York (1991), incorporated herein by reference. Examples of carboxylic acid protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides including N,N-dimethyl, 7-nitroindolyl, hydrazide, N-phenylhydrazide, and the like. Especially preferred carboxylic acid protecting groups are tert-butyl and benzyl.

"Hydroxy protecting group" means an easily removable group which is known in the art to protect a hydroxy group against undesirable reaction during synthetic procedures and to be selectively removable. The use of hydroxy protecting groups is well known in the art and many such protecting groups are known, cf., for example, T. H. Greene and P. G. M. Wuts, Protective Groups in Organic Synthesis, 2nd edition, John Wiley & Sons, New York (1991), incorporated herein by reference. Examples of hydroxy protecting groups include ethers such as methyl; substituted methyl ethers such as methoxymethyl (MOM), methylthiomethyl (MTM), 2-methoxyethoxymethyl (MEM), bis(2-chloroethoxy) methyl, tetrahydropyranyl (THP), tetrahydrothiopyranyl, 4-methoxytetrahydropyranyl, 4-methoxytetrahydrothiopyranyl, tetrahydrofuranyl, tetrahydrothiofuranyl, and the like; substituted ethyl ethers such as 1-ethoxyethyl, 1-methyl-1-methoxyethyl, 2-(phenylselenyl)ethyl, t-butyl, allyl, benzyl, o-nitrobenzyl, triphenylmethyl, a-naphthyldiphenylmethyl, p-methoxyphenyldiphenylmethyl, 9-(9-phenyl-10-oxo) anthranyl (tritylone), and the like; silyl ethers such as trimethylsilyl (TMS), isopropyldimethylsilyl, t-butyldimethylsilyl (TBDMS), t-butyldiphenylsilyl, tribenzylsilyl, tri-p-xylylsilyl, triisopropylsilyl, and the like; esters such as formate, acetate, trichloroacetate, phenoxyacetate, isobutyrate, pivaloate, adamantoate, benzoate, 2,4,6-trimethylbenzoate, and the like; and carbonates such as methyl, 2,2,2-trichloroethyl, allyl, p-nitrophenyl, benzyl, p-nitrobenzyl, S-benzyl thiocarbonate, and the like.

"Amino acid" means an amino acid selected from the group consisting of natural and unnatural amino acids as defined herein.

"Natural amino acid" means an α-amino acid selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural α-amino acids as indicated above; aminobutyric acid (Aib), 3-aminoisobutyric acid (bAib), norvaline (Nva), β-Ala, 2-aminoadipic acid (Aad), 3-aminoadipic acid (bAad), 2-aminobutyric acid (Abu), γ-aminobutyric acid (Gaba), 6-aminocaproic acid (Acp), 2,4-diaminobutryic acid (Dbu), α-aminopimelic acid, trimethylsilyl-Ala (TMSA), allo-isoleucine (aIle), norleucine (Nle), tert-Leu, citrulline (Cit), ornithine (Orn), 2,2'-diaminopimelic acid) (Dpm), 2,3-diaminopropionic acid (Dpr), α- or β-Nal, cyclohexyl-Ala (Cha), hydroxyproline, sarcosine (Sar), and the like; cyclic amino acids; $N^α$-alkylated amino acids such as $N^α$-methylglycine (MeGly), $N^α$-ethylglycine (EtGly) and $N^α$-ethylasparagine (EtAsn); and amino acids in which the α-carbon bears two side-chain substituents.

"Peptide" and "polypeptide" mean a polymer in which the monomers are natural or unnatural amino acid residues joined together through amide bonds. The term "peptide backbone" means the series of amide bonds through which the amino acid residues are joined. The term "amino acid residue" means the individual amino acid units incorporated into the peptides or polypeptides.

"Aliphatic" means a radical derived from a non aromatic C—H bond by removal of the hydrogen atom. The aliphatic radical may be further substituted by additional aliphatic or aromatic radicals as defined herein. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like. "Aliphatic", as used herein, also encompasses the residual, non-carboxyl portion of natural and unnatural amino acids as defined herein.

"Aromatic" means a radical derived from an aromatic C—H bond by removal of the hydrogen atom. Aromatic includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acyl" means an H—CO— or alkyl-CO— group wherein the alkyl group is as herein described. Preferred acyls contain a lower alkyl. Representative acyl groups include formyl, acetyl, propanoyl, 2-methylpropanoyl, butanoyl and palmitoyl.

"Acylamino" is an acyl-NH— group wherein acyl is as defined herein.

"Alkenoyl" means an alkenyl-CO— group wherein alkenyl is as defined herein.

"Alkenyl" means a straight or branched aliphatic hydrocarbon group of 2 to about 15 carbon atoms which contains at least one carbon-carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O— group wherein the alkenyl group is as herein described. Representative alkenyloxy groups include allyloxy or 3-butenyloxy.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" means an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxyalkoxy" means an alkyl-O-alkylene-O— group. Representative alkoxyalkoxy include methoxymethoxy, methoxyethoxy, ethoxyethoxy, and the like.

"Alkoxycarbonyl" means an ester group; i.e. an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" means an alkyl-O-CO-alkylene- group wherein alkyl and alkylene are as defined herein. Representative alkoxycarbonylalkyl include methoxycarbonylmethyl, and ethoxycarbonylmethyl, methoxycarbonyl ethyl, and the like.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl is optionally substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, and pyridylmethyloxycarbonylmethyl.

"Alkylene" means a straight or branched bivalent hydrocarbon chain of 1 to about 6 carbon atoms. The alkylene is optionally substituted with one or more "alkylene group substituents" which may be the same or different, and include halo, cycloalkyl, hydroxy, alkoxy, carbamoyl, carboxy, cyano, aryl, heteroaryl or oxo. Preferred alkylene groups are the lower alkylene groups having 1 to about 4 carbon atoms. Representative alkylene groups include methylene, ethylene, and the like.

"Alkenylene" means a straight or branched bivalent hydrocarbon chain containing at least one carbon-carbon double bond. The alkenylene is optionally substituted with one or more "alkylene group substituents" as defined herein. Representative alkenylene include —CH═CH—, —CH$_2$CH═CH—, —C(CH$_3$)═CH—, —CH$_2$CH═CHCH$_2$—, and the like.

"Alkynylene" means a straight or branched bivalent hydrocarbon chain containing at least one carbon-carbon triple bond. The alkynylene is optionally substituted with one or more "alkylene group substituents" as defined herein. Representative alkynylene include —CH≡CH—, —CH≡CH—CH$_2$—, —CH≡CH—CH(CH$_3$)—, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$-group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon-carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O— group wherein the alkynyl group is defined herein. Representative alkynyloxy groups include propynyloxy, 3-butynyloxy, and the like.

"Alkynyloxyalkyl" means alkynyl-O-alkylene- group wherein alkynyl and alkylene are defined herein.

"Amidino" or "amidine" means a group of formula

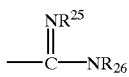

wherein R$^{25}$ is hydrogen; R$^{27}$O$_2$C— wherein R$^{27}$ is hydrogen, alkyl, aralkyl or heteroaralkyl; R$^{27}$O—; R$^{27}$C(O)—; cyano; alkyl nitro; or amino, and R$^{26}$ is selected from hydrogen; alkyl; aralkyl; and heteroaralkyl.

"Amino" means a group of formula Y$^1$Y$^2$N— wherein Y$^1$ and Y2 are independently hydrogen; acyl; or alkyl, or Y$^1$ and Y2 taken together with the N through which Y$^1$ and Y2 are linked form a 4 to 7 membered azaheterocyclyl. Representative amino groups include amino (H$_2$N—), methylamino, dimethylamino, diethylamino, and the like.

"Aminoalkyl" means an amino-alkylene- group wherein amino and alkylene are defined herein. Representative aminoalkyl groups include aminomethyl, aminoethyl, dimethylaminomethyl, and the like.

"Aralkenyl" means a aryl-alkenylene- group wherein aryl and alkenylene are define herein. Preferred aralkenyls contain a lower alkenylene moiety. A representative aralkenyl group is 2-phenethenyl.

"Aralkyloxy" means an aralkyl-O— group wherein aralkyl is defined herein. Representative aralkoxy groups include benzyloxy, naphth-1-ylmethoxy, naphth-2-ylmethoxy, and the like.

"Aralkyloxyalkyl" means an aralkyl-O-alkylene- group wherein aralkyl and alkylene are defined herein. A representative aralkyloxyalkyl group is benzyloxyethyl.

"Aralkyloxycarbonyl" means an aralkyl-O—CO— group wherein aralkyl is defined herein. A representative aralkoxycarbonyl group is benzyloxycarbonyl.

"Aralkyloxycarbonylalkyl" means an aralkoxycarbonyl-alkylene- wherein aralkyloxycarbonyl and alkylene are defined herein. Representative aralkoxycarbonylalkyls include benzyloxycarbonylmethyl, benzyloxycarbonylethyl.

"Aralkyl" means an aryl-alkylene-wherein aryl and alkylene are defined herein. Preferred aralkyls contain a lower alkylene moiety. Representative aralkyl groups include benzyl, 2-phenethyl, naphthlenemethyl, and the like.

"Aralkyloxyalkenyl" means an aralkyl-O-alkenylene- group wherein aralkyl and alkenylene are defined herein. A representative aralkyloxyalkenyl group is 3-benzyloxyallyl.

"Aralkylsulfonyl" means an aralkyl-SO$_2$— group wherein aralkyl is defined herein.

"Aralkylsulfinyl" means an aralkyl-SO— group wherein aralkyl is defined herein.

"Aralkylthio" means an aralkyl-S— group wherein aralkyl is defined herein. A representative aralkylthio group is benzylthio.

"Aroyl" means an aryl-CO— group wherein aryl is defined herein. R epresentative aroyl include benzoyl, naphth-1-oyl and naphth-2-oyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like. The prefix spiro before cycloalkyl means that geminal substituents on a carbon atom are replaced to form 1, 1-cycloalkyl. "Cycloalkylene" means a bivalent cycloalkyl having about 4 to about 8 carbon atoms. Preferred cycloalkylenyl groups include 1,2-, 1,3-, or 1,4-cis or trans-cyclohexylene.

"Cycloalkenyl" means a non-aromatic mono- or multicyclic ring system of about 3 to about 10 carbon atoms, preferably of about 5 to about 10 carbon atoms which contains at least one carbon-carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Heterocyclenyl" means a non-aromatic monocyclic or multicyclic ring system of about 3 to about ring atoms, preferably about 5 to about 10 ring atoms, in which one or more of the atoms in the ring system is/are element(s) other than carbon, for example nitrogen, oxygen or sulfur atoms, and which contains at least one carbon-carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom respectively is present as a ring atom. The heterocyclenyl is optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aryl" means an aromatic monocyclic or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl and naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide, 1,4-benzodioxane, indolinyl, 1,2,3,4-tetrahydroisoquinoline, 1,2,3,4-tetrahydroquinoline, 1 H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon atom.

"Fused heterocyclylaryl" means a radical derived from a fused aryheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. Representative fused cycloalkenylheteroaryl are as described herein for fused heteroarylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinol inyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of about 5 to about 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-nap 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon atom.

"Fused heterocyclenylheteroaryl" means a radical derived from a fused heteroarylheterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to about 6 ring atoms and the heterocyclyl consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol [3,4-b]quinolin-2-yl, 1,2,3,4-tetrahydrobenz [b][1,7] naphthyridin-2-yl, 1,2,3,4-tetrahydrobenz [b][1,6] naphthyridin-2-yl, 1,2,3,4-tetrahydro-9H-pyrido[3,4-b] indol-2-yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1,7]napthyridinyl, 1,2,3,4-tetrahydro[1,8]napthyridinyl, 1,2,3,4-tetrahydro[2,6]napthyridinyl, and the like, in which the bond to the parent moiety is through a non-aromatic carbon atom.

"Fused heterocyclylheteroaryl" means a radical derived from a fused heteroarylheterocyclyl as defined herein, by removal of a hydrogen atom from the heteroaryl portion. Representative fused heterocyclylheteroaryl are as described herein for fused heteroarylheterocyclyl, except that the bond to the parent moiety is through an aromatic carbon atom.

"Aralkynyl" means an aryl-alkynylene- group wherein aryl and alkynylene are defined herein. Representative aralkynyl groups include phenylacetylenyl and 3-phenylbut-2-ynyl.

"Aryldiazo" means an aryl-N=N— group wherein aryl is defined herein. Representative aryldiazo groups include phenyldiazo and naphthyldiazo.

"Arylcarbamoyl" means an aryl-NHCO— group, wherein aryl is defined herein.

"Benzyl" means a phenyl—CH$_2$— group. Substituted benzyl means a benzyl group in which the phenyl ring is substituted with one or more ring system substituents. Representative benzyl include 4-bromobenzyl, 4-methoxybenzyl, 2,4-dimethoxybenzyl, and the like.

"Carbamoyl" means a group of formula Y$^1$Y$^2$NCO— wherein Y$^1$ and Y$^2$ are defined herein. Representative carbamoyl groups include carbamyl (H$^2$NCO—), dimethylaminocarbamoyl (Me$^2$NCO—), and the like.

"Carboxy" and "carboxyl" mean a HO(O)C— group (i.e. a carboxylic acid).

"Carboxyalkyl" means a HO(O)C-alkylene- group wherein alkylene is defined herein. Representative carboxyalkyls include carboxymethyl and carboxyethyl.

"Cycloalkyloxy" means a cycloalkyl-O— group wherein cycloalkyl is defined herein. Representative cycloalkyloxy groups include cyclopentyloxy, cyclohexyloxy, and the like.

"Diazo" means a bivalent —N=N— radical.

"Ethylenyl" means a —CH=CH— group.

"Halo" or "halogen" mean fluoro, chloro, bromo, or iodo.

"Heteroaralkenyl" means a heteroaryl-alkenylene- group wherein heteroaryl and alkenylene are defined herein. Preferred heteroaralkenyls contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene- group wherein heteroaryl and alkylene are defined herein. Preferred heteroaralkyls contain a lower alkylene group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is defined herein. A representative heteroaralkyloxy group is 4-pyridylmethyloxy.

"Heteroaralkyloxyalkenyl" means a heteroaralkyl-O-alkenylene- group wherein heteroaralkyl and alkenylene are defined herein. A representative heteroaralkyloxyalkenyl group is 4-pyridylmethyloxyallyl.

"Heteroaralkyloxyalkyl" means a heteroaralkyl-O-alkylene- group wherein heteroaralkyl and alkylene are defined herein. A representative heteroaralkyloxy group is 4-pyridylmethyloxyethyl.

"Heteroaralkynyl" means an heteroaryl-alkynylene- group wherein heteroaryl and alkynylene are defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is defined herein. Representative heteroaroyl groups include thiophenoyl, nicotinoyl, pyrrol-2-ylcarbonyl, pyridinoyl, and the like.

"Heteroaryldiazo" means an heteroaryl-N=N— group wherein heteroaryl is as defined herein.

"Heteroarylsulphonylcarbamoyl" means a heteroaryl-SO$_2$—NH—CO— group wherein heteroaryl is defined herein.

"Heterocyclylalkyl" means a heterocyclyl-alkylene- group wherein heterocyclyl and alkylene are defined herein. Preferred heterocyclylalkyls contain a lower alkylene moiety. A representative heteroaralkyl group is tetrahydropyranylmethyl.

"Heterocyclylalkyloxyalkyl" means a heterocyclylalkyl-O-alkylene group wherein heterocyclylalkyl and alkylene are defined herein. A representative heterocyclylalkyloxyalkyl group is tetrahydropyranylmethyloxymethyl.

"Heterocyclyloxy" means a heterocyclyl-O— group wherein heterocyclyl is defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"N-oxide" means a

group.

"Oxo" means a group of formula >C=O (i.e., a carbonyl group).

"Phenoxy" means a phenyl-O— group wherein the phenyl ring is optionally substituted with one or more ring system substituents as defined herein.

"Phenylene" means a -phenyl- group wherein the phenyl ring is optionally substituted with one or more ring system substituents as defined herein.

"Phenylthio" means a phenyl-S— group wherein the phenyl ring is optionaljy substituted with one or more ring system substituents as defined herein.

"Pyridyloxy" means a pyridyl-O— group wherein the pyridyl ring is optionally substituted with one or more ring system substituents as defined herein.

"Ring system substituent" means a substituent which optionally replaces a hydrogen CH or NH constituent of an aromatic or non-aromatic ring system. Ring system substituents are selected from the group consisting of aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylbio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2Y$ N—, $Y^1Y^2$N-alkyl—, $Y^1Y^2$NCO— or $Y^1Y^2$NSO$_2$—, wherein $Y^1$ and $Y^2$ independently hydrogen, alkyl, aryl, and aralkyl, or where the substituent is $Y^1Y^2$N— or $Y^1Y^2$N-alkyl— then one of $Y^1$ and $Y^2$ is acyl or aroyl and the other of $Y^1$ and $Y^2$ is hydrogen, alkyl, aryl, and aralkyl. When a ring system is saturated or partially saturated, the "ring system substituent" further comprises methylene (H2C=), oxo (O=) and thioxo (S=).

"Sulfamoyl" means a group of formula $Y^1Y^2$NSO$_2$— wherein $Y^1$ and $Y^2$ are defined herein. Representative sulfamoyl groups are sulfamoyl (H$_2$NSO$_2$—) and dimethylsulfamoyl (Me2NSO2—).

Preferred Embodiments

The preparation of the functionalized resin wherein Y is OH is shown in Scheme 1. It is understood that the methods described in the following schemes for amino resin apply equally to aminomethyl resin. R and A are as defined above.

Scheme 1

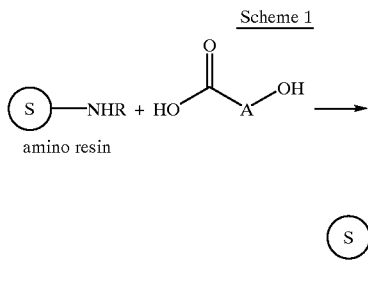

amino resin

According to the foregoing Scheme 1, amino resin is coupled with a carboxylic acid derivative of formula HO$_2$C—A—OH in a suitable organic solvent such as dichloromethane, DMSO or THF. Coupling times range from about 2 to about 12 hours, depending upon the amino resin and carboxylic acid derivative to be coupled, activating agent, solvent and temperature. The coupling is accomplished at from about –10° C. to about 50° C., preferably at about ambient temperature. The carboxylic acid moiety is activated with an appropriate activating agent such as isopropyl chloroformate in the presence of N-methylpiperidine, diisopropylcarbodiimide (DIC) in the presence of 1-hydroxybenzotriazole (HOBT), bis(2-oxo-3-oxazolidinyl)-phosphonic chloride (BOP-C1) in the presence of triethylamine, 2-(1H-benzotriazole-1-yl)-1.1.3.3-tetramethyluronium tetrafluoroborate (TBTU) in the presence of diisopropylethyl amine, N-hydroxysuccinimide in the presence of dicyclohexylcarbodiimide (DCC), and the like.

A preferred resin for preparing the functionalized resins of this invention is aminomethyl polystyrene. Aminomethyl polystyrene wherein R is H or CH$_3$ is more preferred. Aminomethyl polystyrene wherein R is H is most preferred. Depending on the size of the particles, (200 or 400 mesh), aminomethyl resin has loading ranges of from about 0.5 to about 1.2 mmol/g and from about 0.1 to about 0.5 mmol/g, respectively.

In a preferred embodiment, the carboxylic acid derivative HO$_2$C—A—OH is added to a mixture of aminomethyl polystyrene, diisopropylcarbodiimide (DIC) and 1-hydroxybenzotriazole (HOBT) in anhydrous DMF at about ambient temperature and the mixture is stirred for about 4 hours. The functionalized aminomethyl resin 1 is then filtered, washed with one or more solvents and dried.

A preferred functionalized resin has formula I wherein A is

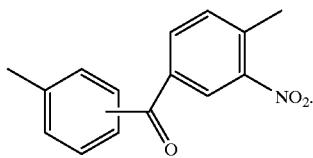

Another preferred functionalized resin has formula 1 wherein A is

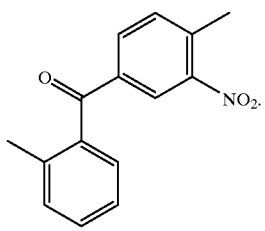

Another preferred functionalized resin has formula 1 wherein A is

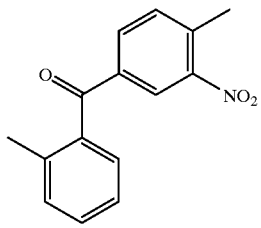

and R is H or methyl.

Another preferred functionalized resin has formula III wherein R is H or methyl and Y is OH or OCOR$^1$.

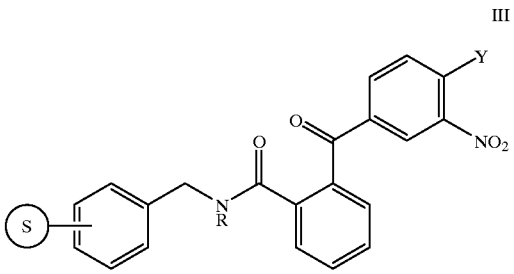

Another preferred functionalized resin has formula III wherein R is H.

The conversion of the functionalized resin wherein Y is OH to the resin-bound activated ester wherein Y is OCOR$^1$ is shown in Scheme 2. In Scheme 2, R$^1$ represents any aliphatic or aromatic group amenable to coupling with the functionalized resin using the solvents and reagents described herein. The group R$^1$ may be further substituted and may contain functional groups suitable for further chemical transformations while attached to the resin. It is understood that when these functional groups possess reactivity such that they could potentially interfere with the coupling reaction and the subsequent cleavage reaction described below, such functional groups should be suitably protected. For a comprehensive treatise on the protection and deprotection of common functional groups see T. H. Greene and P. G. M. Wuts, Protective Groups in Organic Synthesis, 2nd edition, John Wiley & Sons, New York (1991), incorporated herein by reference.

Scheme 2

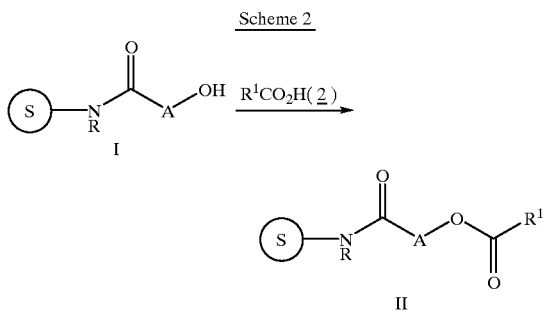

According to the foregoing Scheme 2, carboxylic acid 2 is coupled to the functionalized resin I using the coupling conditions described in Scheme 1 above to form the resin-bound activated ester II. Coupling times range from about 2 to about 24 hours depending on the nature of the functionalized amino resin I, carboxylic acid 2, solvent, reaction temperature and activating agent. Coupling is preferably accomplished using diisopropylcarbodiimide (DIC) in the presence of 1-hydroxybenzotriazole (HOBT) in anhydrous dimethylformamide at about ambient temperature over about 24 hours. The resin-bound activated ester II is then washed with a suitable organic solvent or solvents to remove excess reagents. The resin-bound activated ester II may be dried and stored for future use or is used directly in subsequent reactions.

The cleavage of the resin-bound activated ester II with an amine is shown in Scheme 3. In Scheme 3, $R^2$ and $R^3$ represent independently H or any aliphatic or aromatic group amenable to reaction with the carbonyl moiety of the activated ester to effect the cleavage reaction described below using the solvents and reagents described herein.

Scheme 3

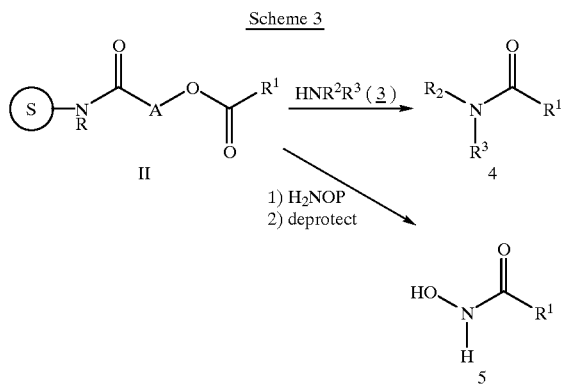

As shown in Scheme 3, the resin-bound activated ester II is cleaved by reaction with an amine of formula 3 in a suitable organic solvent, preferably dichloromethane, dichloroethane or dimethylformamide at from about 20° C. to about 60° C. to prepare the amide 4. The reaction temperature and amount of time required for the cleavage reaction depends on the nature of the substituents $R^2$ and $R^3$. When one of $R^2$ and $R^3$ is H and the other of $R^2$ and $R^3$ is aliphatic, cleavage is accomplished at ambient temperature over about 2 to about 24 hours. When at least one of $R^2$ and $R^3$ is aromatic, elevated temperatures, preferably from about 50 to about 60° C. and reaction times of up to 6 days are required. A catalyst such as 4-dimethylaminopyridine may also be added to accelerate the cleavage reaction.

In a similar manner, the resin-bound activated ester II is cleaved by reaction with a hydroxylamine of formula $H_2NOP$ wherein P is a hydroxy protecting group. Removal of the hydroxy protecting group provides the hydroxamic acid 5.

The functionalized resin of this invention is also useful for the preparation of peptides. In general, this method involves coupling the carboxyl group of a suitably N-protected first amino acid to the resin to form the resin-bound N-protected activated ester, followed by cleavage of the resin-bound activated ester with a carboxy protected second amino acid to form a dipeptide which is protected at the carboxy and N termini.

If desired, a third amino acid is added by removing the N-protection from the dipeptide prepared as described above to form the carboxy protected dipeptide and cleaving a resin-bound activated ester of the third amino acid (suitably N-protected) to form the tripeptide which is protected at the carboxy and N termini. This process is then repeated until the desired amino acid residues have been incorporated in the peptide.

Alternatively, peptides comprising multiple amino acids are prepared by coupling a suitably N-protected peptide subunit comprising two or more amino acids to the functionalized resin to form the resin-bound N-protected peptide activated ester, and cleaving the resin-bound activated ester with a carboxy protected amino acid or second peptide subunit. Thus, in addition to the sequential addition of amino acids described above, a polypeptide may be prepared using the functionalized resin of this invention by coupling a N-protected peptide to the resin and cleaving the N-protected peptide activated ester with a carboxy protected amino acid or peptide, or by coupling a N-protected amino acid to the functionalized resin and cleaving the resin-bound N-protected amino acid activated ester with a carboxy protected peptide.

N-protecting groups suitable for use in peptide synthesis using the functionalized resin of this invention should have the properties of being stable to the conditions of coupling to the functionalized resin and cleavage of the resin-bound activated ester, while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, (α,α)dimethyl-3,5-dimethoxybenzyloxycarbonyl, o-nitrophenylsulfenyl, 2-cyano-t-butyloxycarbonyl, and the like.

Carboxy protecting groups suitable for use in peptide synthesis using the functionalized resin of this invention should have the properties of being stable to cleavage of the resin-bound activated ester, while being readily removable without destruction of the growing peptide chain or racemization of any of the chiral centers contained therein. Examples of carboxy protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides including N,N-dimethyl, 7-nitroindolyl, hydrazide, N-phenylhydrazide, and the like. Especially preferred carboxylic acid protecting groups are tert-butyl and benzyl.

The functionalized resin of this invention is also useful for the parallel synthesis of a multiplicity of different amide, peptide or hydroxamic acid end products as outlined in Schemes 4a and 4b below. In Schemes 4a and 4b, $R^4$–$R^1$ represent, independently, an aliphatic or aromatic group as defined herein. $R^8$–$R^{15}$ represent, independently, H or an aliphatic or aromatic group amenable to reaction with the carbonyl moiety of the resin-bound activated ester to effect the cleavage reaction described herein using the solvents and reagents described herein.

The parallel synthesis of 4 amides or peptides having variable N-substituents is outlined in Scheme 4b above.

Scheme 4a

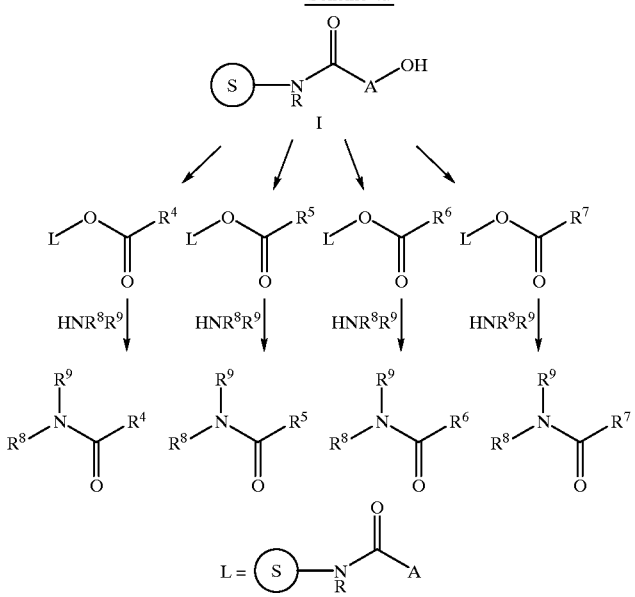

The parallel synthesis of a multiplicity of amides or peptides bearing variable carbonyl group substituents is illustrated using 4 carboxylic acid compounds and a single amine $HNR^8R^9$ in Scheme 4a. According to Scheme 4a, the functionalized resin of this invention is divided into 4 portions. Each portion of resin is then coupled with a different carboxylic acid compound to give 4 portions of resin-bound activated ester. Each portion of resin-bound activated ester is then cleaved with an amine (or amino acid) of formula $HNR^8R^9$ to give 4 portions of amide derived from a single amine but having different carbonyl group substituents.

According to Scheme 4b, the functionalized resin of this invention is coupled with a carboxylic acid of formula $R^4CO_2H$. The resulting resin-bound activated ester is then divided into 4 portions, and each portion of resin-bound activated ester is then cleaved with a different amine (or amino acid) to give the 4 amides (or peptides) shown above which possess a common carboxylic acid substituent and different nitrogen substituents.

The functionalized resins of this invention are also useful for constructing a combinatorial library of amides or peptides as illustrated for the simple library prepared from 4-carboxylic acids and 4 amines as outlined in Scheme 5.

Scheme 4b

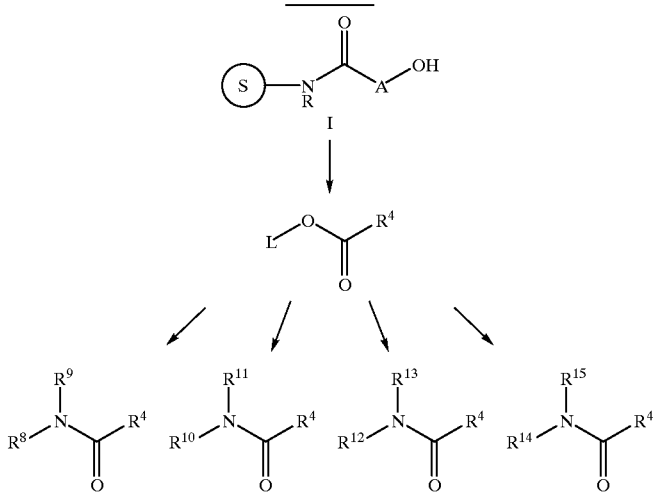

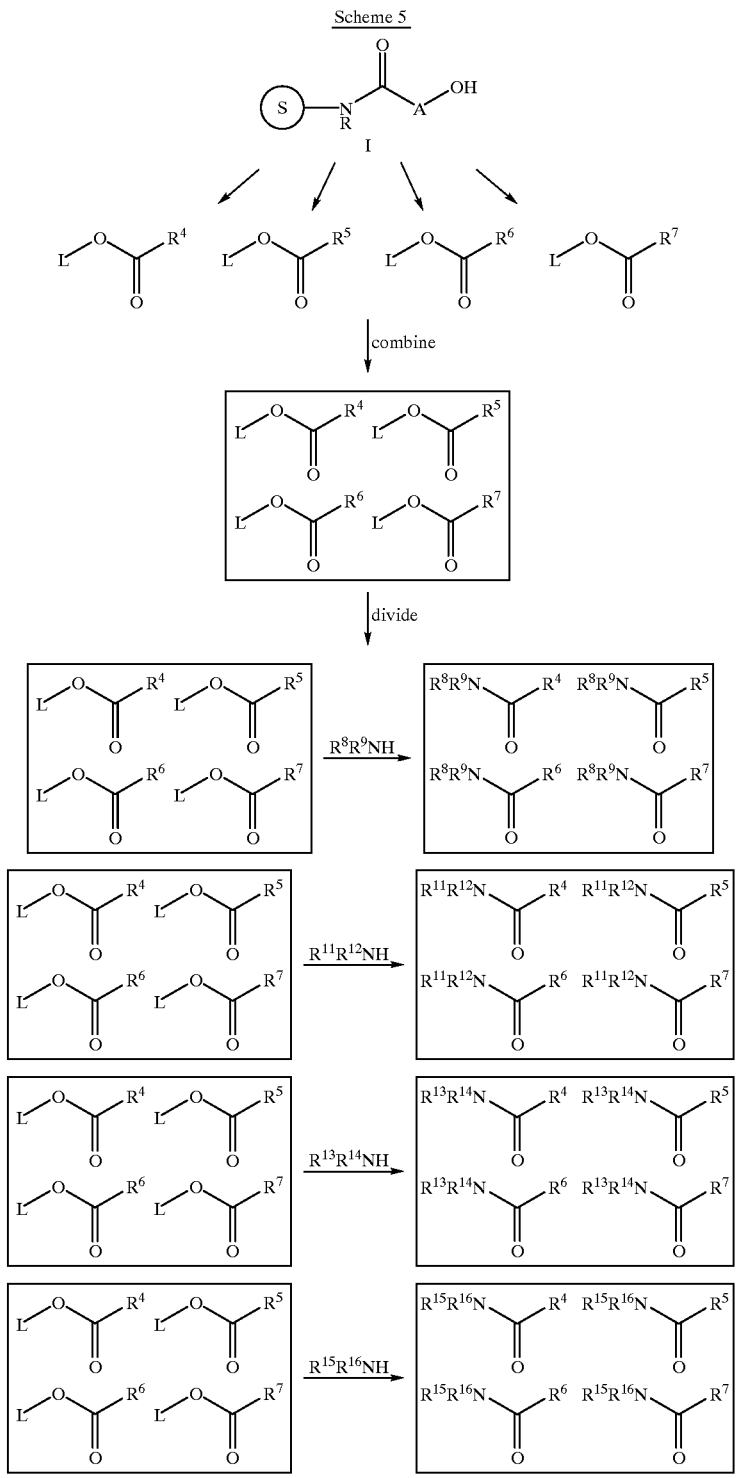

Scheme 5

According to the foregoing Scheme 5, the functionalized resin is divided in 4 portions, and each portion is coupled with a different carboxylic acid compound to prepare 4 different resin-bound activated ester compounds. The resin-bound activated ester compounds are then mixed together to form a single portion which is divided into 4 portions of resin-bound activated ester, in which each portion contains approximately equal amounts of each individual resin-bound activated ester compound. Each of the 4 portions is then cleaved with a different amine to give 4 portions of amide, each of which contains 4 compounds representing the products of cleavage of the 4-different resin-bound activated ester compounds with a single amine. In this manner a combinatorial library containing a multiplicity of amides may be quickly constructed. In a similar manner, a combinatorial library of peptides may be assembled by repeating the dividing-recombining sequence for each amino acid or peptide building block.

The methodology described above for solid phase synthesis on resins is readily extended to synthesis on pins wherein the pins comprise a detachable polyethylene- or polyproylene-base head and an inert stem. The heads are grafted with an amino functionalized methacrylate copolymer on which the synthesis takes place. Synthesis on pins offers several advantages over resin-based solid phase synthesis techniques because it readily lends itself to automation and reduces the handling difficulties associated with conventional resin-based solid phase synthesis. Synthesis on pins is especially useful for the rapid construction of combinatorial libraries of amides or peptides. Solid phase synthesis pins is described in Technical Manual, Multipin™ SPOC, Chiron Technologies (1995) and references therein.

The preparation of amides on amino-functionalized pins is outlined in Scheme 4. In Scheme 4,

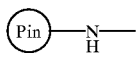

represents the polyethylene or polypropylene head described above on which is grafted a methacrylic acid-dimethylacrylamide copolymer substituted with a plurality of amino groups. The Fmoc-protected functionalized pin 5 is available from Chiron Technologies, San Diego, Calif.

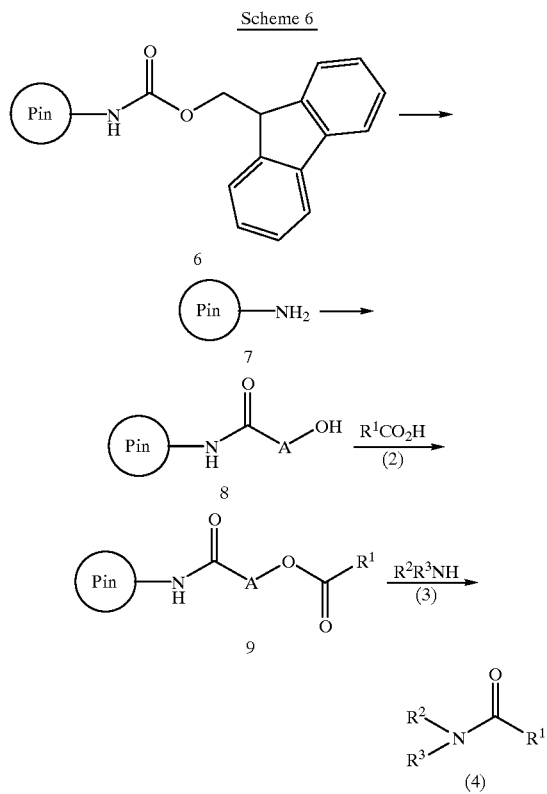

According to the foregoing Scheme 6, the Fmoc protected amino polymer 6 is deprotected by treatment with a basic amine, preferably 20% piperidine/dimethylformamide or 2% DBU/dimethylformamide. The free amino polymer 7 is functionalized by coupling with a carboxylic acid compound of formula $HO^2C$—A—OH wherein A is defined above, for example using 1-hydroxybenzotriazole (HOBT) in the presence of N-methylmorpholine (NMM), diisopropylcarbodiimide (DIC) in the presence of HOBT or dicyclohexylcarbodiimide (DCC) in the presence of HOBT in a suitable solvent such as dichloromethane, dimethylformamide (DMF), N-methylpyrrolidone (NMP), or dichloromethane/DMF mixtures to prepare the functionalized pins 8. Coupling of 8 with carboxylic acid compound 2 to form the polymer bound activated ester 9, followed by cleavage with amine 3 to provide amide 4 proceeds as described in Schemes 2 and 3 above.

It is to be understood that this invention covers all appropriate combinations of the particular and preferred groupings referred to herein.

The foregoing may be better understood by reference to the following examples, which are presented for illustration and are not intended to limit the scope of this invention.

EXAMPLE 1

Preparation of 2-(4-hydroxy-3-nitrobenzoyl)benzamide methyl resin.

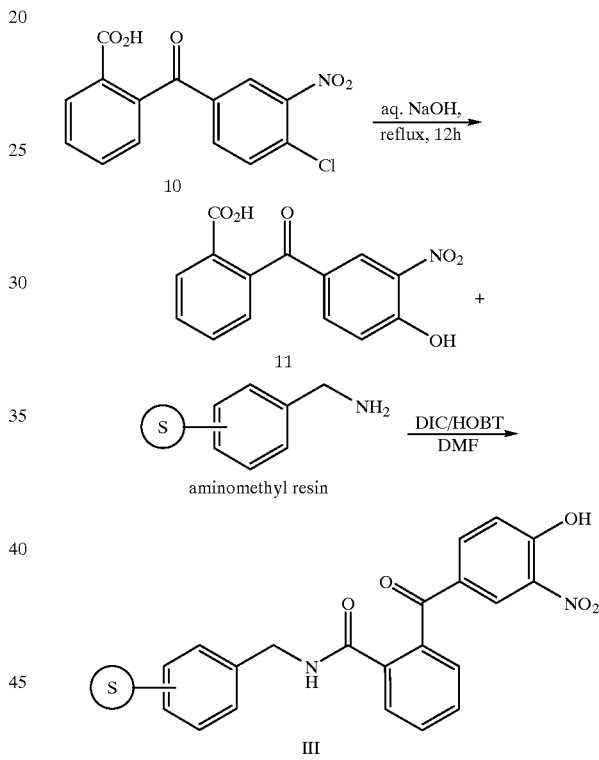

Aminomethyl resin (Calbiochem-Novabiochem Corp. San Diego, Calif.; 1 g, loading=0.39 mmol/g) is swollen in 10 ml of anhydrous dimethylformamide. After 10 minutes 50 mg of 1-hydroxybenzotriazole (HOBT) (1 eq.) and 0.31 ml of diisopropylcarbodiimide (DIC) (5 eq.) are added, followed by the addition of a solution of 0.56 g of 2-(4-hydroxy-3-nitrobenzoyl)benzoic acid (5 eq.) in 5 ml of anhydrous dimethylformamide. The reaction mixture is smoothly stirred for 4 hours by bubbling with nitrogen, then the resin is filtered and washed 5 times with 5 ml of dimethylformamide; 5 times alternately with 5 ml of methylene chloride and 5 ml of diethyl ether; and finally with methylene chloride. The 2-(4-hydroxy-3-nitrobenzoyl) benzamide methyl resin (1.05 g), obtained as a yellow solid, is dried in a vacuum oven at 35° C. for 4 hours. IR (cm$^{-1}$): 1670 (g C=O, Ar—C=O—Ar); 1538 ($g_{as}$ Ar—NO$_2$) 1348 ($g_s$ Ar—NO$_2$). Elemental analysis (% N): calc. 1.0; found 1.0.

2-(4-hydroxy-3-nitrobenzoyl)benzoic acid is prepared as follows: a mixture of 10.0 g of 2-(4-chloro-3-nitrobenzoyl)benzoic acid, 200 ml of aqueous sodium hydroxide (1.5 M) and 20 ml of dioxane is heated at reflux for 12 hours. After cooling, the mixture is added to 200 ml of 1:1 concentrated sulfuric acid-ice water with stirring. The resulting solid is filtered, washed with water to a pH of about 6 and dried to obtain 9.5 g of 2-(4-hydroxy-3-nitrobenzoyl)benzoic acid as a light yellow solid. MS: (EI 70 eV); M+,(%): 287 (36); 197 (31); 166 (100); 149 (75); 120 (34).

EXAMPLE 2

Preparation of 2-(4-hydroxypyrid-2-yl)benzamide methyl resin.

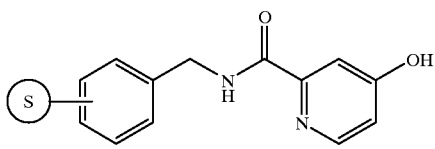

The desired resin is prepared using the procedure of Example 1, except substituting 4-hydroxypyridine-2-carboxylic acid for 2-(4-hydroxy-3-nitrobenzoyl)benzoic acid. The preparation of 4-hydroxypyridine-2-carboxylic acid is described by Ochai, et al. in *Pharm. Bull.*, 2, 137 (1954).

EXAMPLE 3

Preparation of 2-[4-(4-bromophenylacetoxy)-3-nitrobenzoyl]benzamide methyl resin.

The 2-(4-hydroxy-3-nitrobenzoyl)benzamide methyl resin prepared in Example 1 (0.25 g, loading=0.35 mmol/g) is swollen in 2 ml of anhydrous dimethylformamide. After 10 minutes 20 mg of 4-dimethylaminopyridine (DMAP) (2 eq.) and 0.31 ml of diisopropylcarbodiimide (DIC) (5 eq.) are added, followed by a solution of 0.1 g of 4-bromophenylacetic acid (5 eq.) in 1.0 ml of anhydrous dimethylformamide. The reaction mixture is smoothly stirred overnight at ambient temperature and then filtered and washed 5 times with 2 ml of dimethylformamide; 5 times alternately with 2 ml of methylene chloride and 2 ml of diethylether and finally with methylene chloride. 2-[4-(4-bromophenylacetoxy)-3-nitrobenzoyl]benzamide methyl resin 12 (0.26 g) is obtained as a yellow solid and used directly in the cleavage step. IR (cm$^{-1}$): 1778 (g Ph—O—(CO)—CH$_2$—and/or —NH—(CO)—Ph)), 1676 (g C=O, Ar—(CO)—Ar), 1538 ($g_{as}$ Ar—NO$_2$), 1371 ($g_s$ Ar—NO$_2$). Elemental analysis: calculated: N, 0.9; Br, 2.6. Found: N, 0.8; Br, 3.2.

EXAMPLE 4

Cleavage with Aliphatic Amines: Preparation of N-benzyl-2-(4-bromophenyl)acetamide.

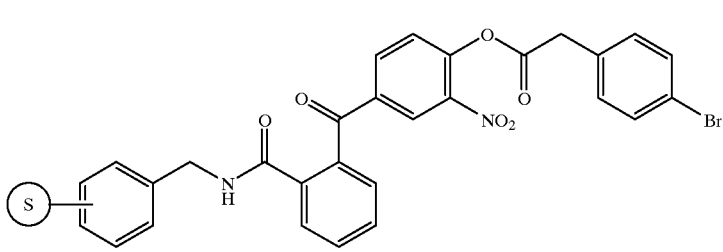

12

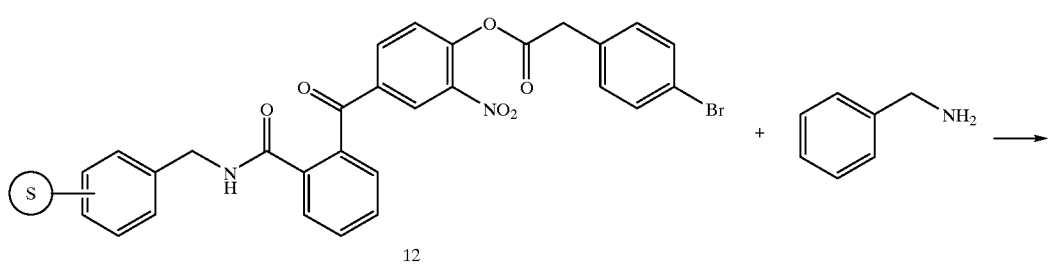

12

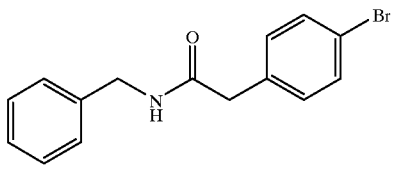

Fifty mg of 2-[4-(4-bromophenylacetoxy)-3-nitrobenzoyl]benzamide methyl resin (loading=0.33 mmol/g) 12, prepared as in Example 3, is swollen in 1 ml of dichloromethane. Then 1.8 ml (1 eq.) of benzylamine is added and the reaction mixture is stirred overnight at ambient temperature. The reaction mixture is filtered and concentrated to give 2.5 mg of N-benzyl-2-(4-bromophenyl)acetamide as a white solid.

EXAMPLE 5

Cleavage with Aromatic amines: Preparation of N-(2-methoxyphenyl)-2-(4-bromophenyl)acetamide.

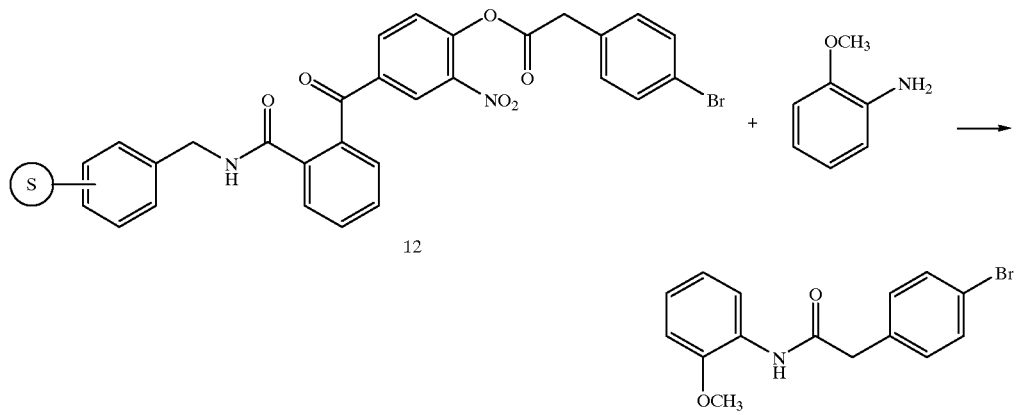

One hundred mg of 2-[4-(4-bromophenylacetoxy)-3-nitrobenzoyl]benzamide methyl resin (loading=0.33 mmol/g) 12, prepared as in Example 3, is swollen in 2 ml of 1,2-dichloroethane. Then 3.7 ml (1 eq.) of o-anisidine and 1 mg (3 eq.) of 4-dimethylaminopyridine (DMAP) are added. The reaction mixture is stirred at 50° C. for 6 days. The reaction mixture is filtered and concentrated to give an oil. LC/MS analysis showed 2 peaks at 220 nm of which the major peak is the expected product (MW 319) and the other the unreacted o-anisidine.

EXAMPLE 6

Preparation of 2-(4-hydroxy-3-nitrobenzoyl)benzamide Functionalized Pins.

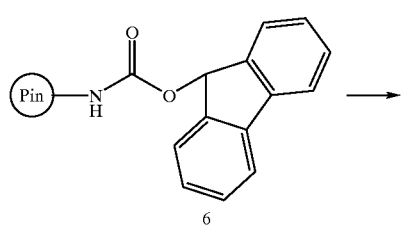

Fmoc protected amino polymer 6 (fixed on a Multipin™ System, Macro Crown (6 μM), available from Chiron Technologies) is deprotected with 20% piperidine/DMF to give the amino polymer 7 which is then converted to the of 2-(4-hydroxy-3-nitrobenzoyl)benzamide functionalized polymer 13 using the method and reagents described in Example 1.

EXAMPLE 7

Preparation of Amides using 2-(4-hydroxy-3-nitrobenzoyl)benzamide Functionalized Pins.

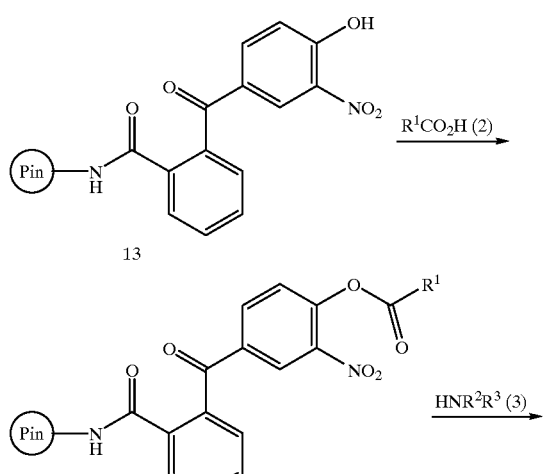

The following amides 4 are prepared by coupling the desired carboxylic acid 2 to the functionalized pins prepared as described in Example 5 using the method of Example 2, followed by cleavage of the activated ester 14 with the desired amine 3 using the method of Examples 3 or 4.

What is claimed is:

1. A functionalized resin of formula

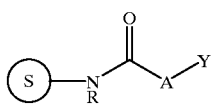

wherein

Ⓢ is a solid support;
R is H or alkyl;
A is selected from

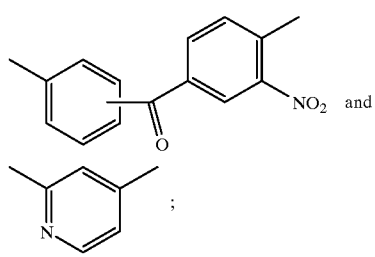

Y is OH or $OCOR^1$; and
$R^1$ is aliphatic or aromatic.

2. The functionalized resin according to claim 1 wherein A is

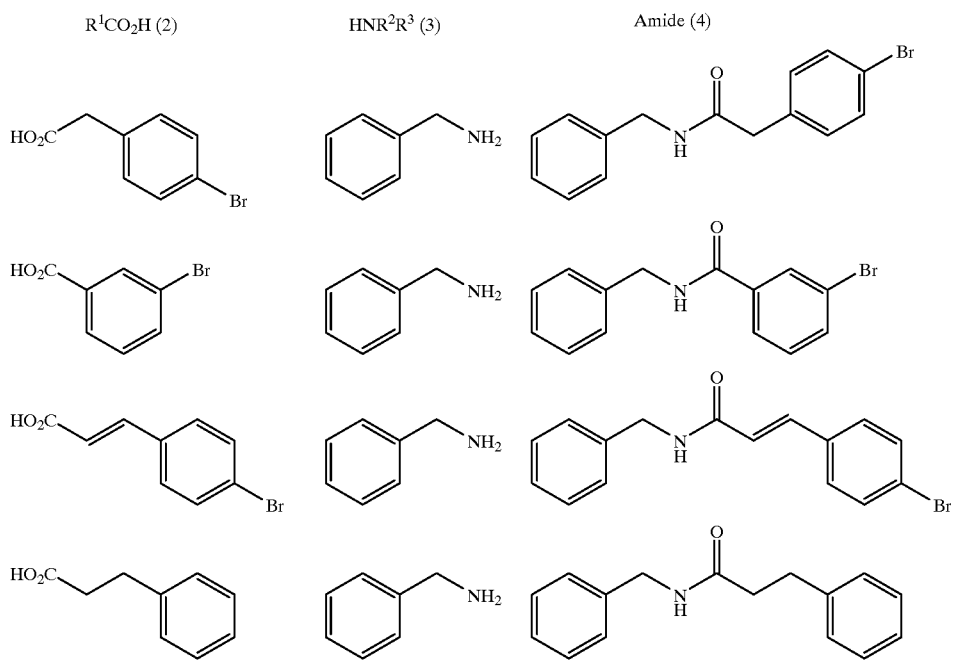

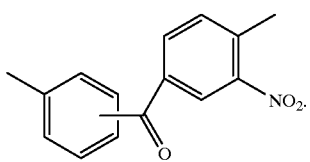

3. The functionalized resin according to claim 2 wherein A is

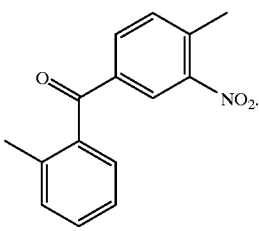

4. The functionalized resin according to claim 3 wherein R is H or methyl.

5. The functionalized resin having the formula

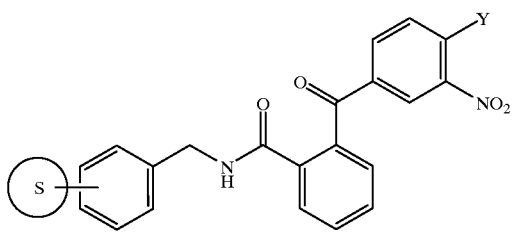

wherein R is H or methyl;
Y is OH or OCOR$^1$;
and R$^1$ is aliphatic or aromatic.

6. The functionalized resin according to claim 5 wherein R is H.

7. The functionalized resin according to claim 1 wherein Y is OH.

8. The functionalized resin according to claim 1 wherein Y is OCOR$^1$.

9. A process for preparing an amide of formula

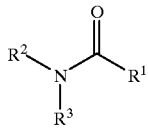

wherein
R$^1$ is aliphatic or aromatic; and
R$^2$ and R$^3$ are independently H, aliphatic or aromatic, comprising reacting a resin-bound activated ester compound of formula

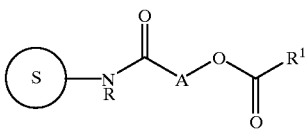

wherein

Ⓢ is a solid support;
R is H or alkyl; and
A is

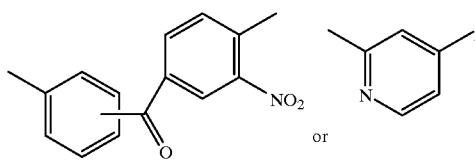

with an amine of formula HNR$^2$R$^3$.

10. The process of claim 9 wherein A is

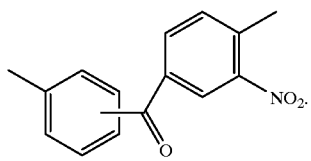

11. The process of claim 9 wherein A is

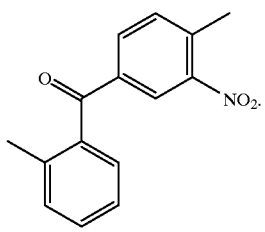

12. The process of claim 10 wherein R is H or methyl.
13. The functionalized resin according to claim 5 wherein Y is OH.
14. The functionalized resin according to claim 4 wherein Y is OH.
15. The functionalized resin according to claim 4 wherein Y is OCOR$^1$.

* * * * *